United States Patent
Prien et al.

(10) Patent No.: US 8,491,593 B2
(45) Date of Patent: Jul. 23, 2013

(54) TARGETING DEVICE FOR ORTHOPEDIC IMPLANTS

(75) Inventors: Ole Prien, Kiel (DE); Helge Giersch, Kiel (DE); Axel Cremer, Fahrenkrog (DE)

(73) Assignee: Stryker Trauma GmbH (DE)

( * ) Notice: Subject to any disclaimer, the term of this patent is extended or adjusted under 35 U.S.C. 154(b) by 1144 days.

(21) Appl. No.: 11/478,791

(22) Filed: Jun. 30, 2006

(65) Prior Publication Data
US 2007/0167953 A1    Jul. 19, 2007

Related U.S. Application Data

(60) Provisional application No. 60/759,376, filed on Jan. 17, 2006.

(30) Foreign Application Priority Data

Apr. 25, 2006  (EP) .................................... 06008537

(51) Int. Cl.
*A61B 17/58* (2006.01)

(52) U.S. Cl.
USPC ................. 606/96; 606/86 R; 606/98; 606/99

(58) Field of Classification Search
USPC .......................... 606/96–99, 86 R, 86 B, 86 A
See application file for complete search history.

(56) References Cited

U.S. PATENT DOCUMENTS

| | | | |
|---|---|---|---|
| 4,945,904 A | 8/1990 | Bolton et al. | |
| 5,423,826 A * | 6/1995 | Coates et al. | 606/96 |
| 5,676,666 A | 10/1997 | Oxland et al. | |
| 5,766,174 A | 6/1998 | Perry | |
| 6,224,601 B1 | 5/2001 | Friedl | |
| 6,235,034 B1 | 5/2001 | Bray | |
| 6,267,763 B1 * | 7/2001 | Castro | 606/86 A |
| 6,989,012 B2 | 1/2006 | Le Huec et al. | |
| 2002/0147450 A1 | 10/2002 | LeHuec et al. | |
| 2003/0135213 A1 * | 7/2003 | LeHuec et al. | 606/69 |

(Continued)

FOREIGN PATENT DOCUMENTS

| | | |
|---|---|---|
| DE | 10131992 | 1/2003 |
| WO | WO-2005/089660 | 9/2005 |

OTHER PUBLICATIONS

"Basic Percutaneous Intrumentation and Aiming Arm for 4.5 mm LCP Condylar Plates", Synthes Technique Guide, pp. 1-27.
"Less Invasive Stabilization System (LISS)", Synthes Technique Guide, Proximal Tibia, pp. 1-32.

(Continued)

*Primary Examiner* — Eduardo C Robert
*Assistant Examiner* — Julianna N Harvey
(74) *Attorney, Agent, or Firm* — Lerner, David, Littenberg, Krumholz & Mentlik, LLP (57) ABSTRACT

A medical system includes parts used in a method for detachably establishing a spatial orientation between a body implant and an aiming device. A positioning arm being connected to the aiming device and an adaptor device being connected to or integrally formed with a bone stabilizing plate are hooked into each other. This is accomplished by means of an engaging element of the positioning arm, which engaging element is designed such that it may be coupled with an attachment element of the adaptor device. Further, there is provided a snapping mechanism which is designed to automatically engage in an interlocking element of the adaptor device, when the positioning arm, when hooked into the adaptor device, is rotated relative to the adaptor device towards a final angular position.

16 Claims, 11 Drawing Sheets

U.S. PATENT DOCUMENTS

| | | | |
|---|---|---|---|
| 2004/0015174 A1* | 1/2004 | Null et al. | 606/99 |
| 2004/0033469 A1 | 2/2004 | Blacklock | |
| 2004/0034356 A1 | 2/2004 | Le Huec et al. | |
| 2004/0204717 A1* | 10/2004 | Fanger et al. | 606/96 |
| 2005/0015093 A1 | 1/2005 | Suh et al. | |
| 2005/0085818 A1 | 4/2005 | Huebner | |
| 2005/0287496 A1 | 12/2005 | Niznick | |
| 2006/0155284 A1* | 7/2006 | Doherty et al. | 606/69 |

OTHER PUBLICATIONS

"Less Invasive Stabilization System (LISS)", Synthes Technique Guide, Distal Femur, pp. 1-36.

Stryker, Internal document concerning developments on the field of osteosynthesis.

Stryker, Surgical Technique.

Office Action from U.S. Appl. No. 11/482,443, mailed Feb. 17, 2010.

* cited by examiner

TARGETING DEVICE FOR ORTHOPEDIC IMPLANTS

CROSS-REFERENCE TO RELATED APPLICATIONS

This application claims the benefit of the filing date of U.S. Provisional Patent Application No. 60/759,376 filed Jan. 17, 2006 and European Patent Application No. 06008537.0 filed Apr. 25, 2006, the disclosures of which are hereby incorporated herein by reference.

BACKGROUND OF THE INVENTION

The present invention relates to the field of surgical instruments. In particular, the present invention relates to a medical system for detachably establishing a spatial orientation between a body implant and an aiming device. More particularly, the present invention relates to a medical system and parts of the system, which allow for a precise establishing of a relative spatial orientation between a bone stabilization implant and an aiming device for anchoring the implant to an internal part of a body.

The invention relates further to a method for detachably establishing a spatial orientation between a body implant and an aiming device, in particular between a bone stabilization implant and an aiming device for anchoring the implant to an internal part of a body.

In order to allow for a reliable stabilization of a broken bone in its normal position, special bone stabilizing implants are frequently used. Such implants are for instance metal plates, which are made e.g. from surgical steel. Plates used for such purposes are usually fixed to the bone parts by means of threaded screws, which are driven into the bone tissue after so-called pre-drilled or pilot-drilled holes have been generated in the bone tissue. These pre-drilled holes allow for a reliable screwing procedure whereby the risk of further destroying the bone with the screw is significantly reduced.

In order to facilitate the drilling of these pre-drilled holes there are known so-called aiming or targeting devices, which work like a drilling jig. Thereby, an aiming or targeting device is detachably fixed to the metal plate in a precise spatial position.

Aiming devices are also used in connection with locking nails, which are driven into the intramedullary canal of the bone. Thereby, the position of a cross bore within the interlocking nail can be determined precisely. The cross bore is adapted to accommodate a fixing screw, which is driven crosswise through the corresponding bone section.

U.S. Pat. No. 6,224,601 B1 discloses the use of an aiming device in an osteosynthesis auxiliary for the treatment of subtrochanteric, peritrochanteric and femoral-neck fractures.

There is a need for a medical system, medical system parts and a method for spatially adjusting an aiming device relative to a body implant, which allow for an easy, quick, reliable and precise relative positioning of an aiming device with respect to a body implant.

SUMMARY OF THE INVENTION

In order to fulfill the need defined above there are provided a body implant, an adaptor device, a medical system and a method for detachably establishing a spatial orientation between a body implant and an aiming device.

According to an aspect of the invention there is provided an adaptor device for detachably establishing a spatial orientation between a body implant and an aiming device, in particular for detachably establishing a spatial orientation between a bone stabilization implant and an aiming device for anchoring the implant to an internal part of a body. The adaptor device comprises an attachment element, which is designed such that an engaging element of a positioning arm can be hooked into the adaptor device. The adaptor device further comprises an interlocking element, which is designed such that a snapping mechanism of the positioning arm automatically engages in the interlocking element when the positioning arm, when hooked into the adaptor device, is rotated relative to the adaptor device towards a final angular position and approaches the final position.

This aspect of the present invention is based on the idea that both a force-fit and a form-fit connection between the adaptor device and the positioning arm can be realized if the positioning arm is swiveled around a predefined center of rotation toward a final angular position.

The form-fit connection may be provided by the contour of the adaptor device, which contour complementarily fits to a contour being provided at the positioning arm. When the snapping mechanism is engaged in the interlocking element, the contour of the adaptor device abuts against the contour of the positioning arm such that a form-fit connection is realized.

The force-fit connection may be provided if the adaptor device comprises a slightly different bending than the corresponding portion of the positioning arm, which portion abuts against the adaptor device when the snapping mechanism is engaged in the interlocking element.

Thereby, the adaptor device and/or the positioning arm are made from a material, which is at least partially resilient. When the form-fit connection between these two parts is established, at least one of these two parts is elastically deformed whereby the deformation force provides for the force-fit connection. Such a force-fit connection has the advantage that there is practically no spatial tolerance between the adaptor device and the positioning arm. Therefore, a very precise spatial positioning between the adaptor device and the positioning arm may be established.

The snapping mechanism of the positioning arm automatically engages in the interlocking element when the positioning arm has approached the final position. In the course of the whole movement the adaptor device is kept hooked into the adaptor device. The rotation is carried out around a rotation axis, which runs through a region wherein the attachment element and the engaging element abut against each other.

The adaptor device is adapted to be connected to a bone stabilizing implant. The adaptor device and the implant may be made of a single piece or of two or more individual pieces. However, it has to be ensured that the adaptor device and the implant may be rigidly fixed to each other.

The positioning arm is adapted to be connected to an aiming device. The positioning arm and the aiming device may be made of a single piece or of two or more individual pieces. In the latter case it has also to be ensured that the positioning arm and the aiming device are rigidly fixed to each other, such that the friction and/or form locked positioning arm provides a mechanically stable platform for the aiming device.

According to an embodiment of the present invention the attachment element is a projection salient from a body of the adaptor device. This may provide the advantage that the adaptor device can be manufactured easily out of a single piece of material.

It has to be noted that the attachment element may be any element, which allows that the positioning arm may be hooked into the adaptor device. For instance the attachment element may also be a recess, into which a projecting engaging element of the positioning arm engages.

According to a further embodiment of the invention the interlocking element comprises an edge. The edge may be resilient such that a rigid or stiff element of the snapping mechanism can engage. Alternatively, the edge may by rigid such that a resilient and/or flexible element of the snapping mechanism can engage. A resilient and/or flexible element may be realized with a flexible material or by means of a spring type element, which prestresses the resilient element.

According to a further embodiment of the invention the adaptor device comprises a further attachment element, which is designed in such a manner that a further engaging element of the positioning arm can be hooked into the further attachment element. This may have the advantage that a mechanically stable three-point bearing is automatically generated when the snapping mechanism of the positioning arm engages in the interlocking element.

Furthermore, when two attachment elements are involved in order to provide a mechanical coupling between the adaptor device and the positioning arm, the rotation axis of the positioning arm is defined precisely by the spatially arrangement of two regions wherein the two attachment elements and the two engaging elements abut against each other, respectively. Therefore, an operator and in particular a surgeon can easily and effectively attach the positioning arm to the adaptor device in a reliable spatial position.

It should be noted that a stable three-point bearing might alternatively be realized by means of only one attachment element but two interlocking elements, the interlocking element described above and a further interlocking element. Thereby, the rotation of the positioning arm is carried out with respect to a center of rotation or a pivotal point such the rotation axis is spatially not exactly defined. However, an operator or a surgeon will have no problem in manually controlling the rotation such that the snapping mechanism will engage in the interlocking element.

According to a further embodiment of the invention the further attachment element is a further projection salient from a body of the adaptor device. As has been described above with regard to the attachment element, also the further attachment element may be a recess, into which a further projecting engaging element engages.

According to a further embodiment of the invention the adaptor device is formed integrally with the implant. This may provide the advantage, that there is no additional effort necessary in order to provide a rigid and mechanically reliable connection between the adaptor device and the implant.

However, it has to be pointed out that as an alternative the adaptor element may also be formed separately from the implant. In this case, one has to ensure that a rigid and mechanically reliable connection between the adaptor device and the implant is provided. This may be done e.g. be using appropriate coupling elements like screws, pins, nails, rivets, et cetera.

According to a further embodiment of the invention the adaptor device is formed integrally with an internal fixator and in particular with a plate, which is used for bone stabilization. Such an internal fixator or such a plate may be used in order to fix a broken bone in its anatomically correct position. Thereby, the plate is attached to different parts of the bone by means of screws, pins, loops, et cetera. In particular when screws are used for attaching the plate, an aiming device may be very helpful, which aiming device comprises a drilling jig. Thereby, an operator and in particular a surgeon is capable of precisely drilling holes in the bone, whereby each hole is formed exactly at the proper position with respect to a corresponding through hole in the plate.

According to a further aspect of the invention there is provided a positioning arm for detachably establishing a spatial orientation between a body implant and an aiming device, in particular for detachably establishing a spatial orientation between a bone stabilization implant and an aiming device for anchoring the implant to an internal part of a body. The positioning arm comprises an engaging element, which is designed in such a manner that it may be coupled to an attachment element of an adaptor device such that the positioning arm is hooked into the adaptor device. The positioning arm further comprises a snapping mechanism, which is designed to automatically engage in an interlocking element of the adaptor device, when the positioning arm, when hooked into the adaptor device, is rotated relative to the adaptor device towards a final angular position.

According to an embodiment of the invention the engaging element is a notch or hook. The notch or hook may be formed directly in the body of the positioning arm. Preferably, the notch is formed in a projection extending from the body of the positioning arm.

According to a further embodiment of the invention the snapping mechanism comprises a hook type element, which is adapted to engage in the interlocking element. Preferably, the hook type element is resilient such that it is capable of engaging in a stiff interlocking element.

However, it should be clear that the positioning arm might also be realized with a stiff or inflexible hook type element, which is adapted to engage in a resilient interlocking element or at least in resilient part of the interlocking element.

A resilient hook type element may be realized with a flexible material or by means of a spring element, which prestresses the hook type element.

According to a further embodiment of the invention the positioning arm comprises a further engaging element, which is designed in such a manner that it may be coupled to a further attachment element of the adaptor device. As has already been mentioned above, the use of a further engaging element in connection with a corresponding further attachment element provides the advantage that the rotation axis of the positioning arm is defined precisely. Furthermore, a mechanically stable three-point bearing is automatically generated when the snapping mechanism of the positioning arm engages in the interlocking element.

In this context it is again noted that as an alternative a stable three-point bearing can be realized with only one attachment element but with two interlocking elements. Thereby, the rotation of the positioning arm is carried out with respect to a center of rotation or a pivotal point. In that case, the orientation of the rotational axis is defined by a single reference point only. This means, that an operator and in particular a surgeon has to take care that the positioning arm is moved properly such that, when reaching the final angular position of the positioning arm, the interlocking element and the snapping mechanism provide a mechanically reliable connection between the adaptor device and the positioning arm.

According to a further embodiment of the invention the further engaging element is a further notch. As has been described above with respect to the attachment element also the further attachment element may be a recess into which a further projecting engaging element engages.

The further notch may be formed in the same manner, in a similar manner or in a different manner with respect to the notch described above. Therefore, the further notch can be formed directly in the body of the positioning arm. Preferably, the further notch is formed in a projection extending from the body of the positioning arm.

According to a further embodiment of the invention the positioning arm further comprises a handle for facilitating a manual rotation of the positioning arm with respect to the adaptor device. Preferably, the handle is formed in an ergonomic manner. This has the advantage that an easy use of the positioning arm is guaranteed even if the surgeon is under a physical and/or under a mental stress condition, which frequently occurs in particular during complicated and elaborate surgeries.

According to a further embodiment of the invention the positioning arm further comprises a locking device, which is adapted to lock the snapping mechanism. The locking device has the advantage that an unintentional opening of the mechanical connection between the snapping mechanism and the interlocking element may be effectively prevented. Of course, the positioning arm may be removed from the adaptor device by an appropriate movement of the locking device after a surgical procedure using the aiming device has been successfully carried out.

According to a further embodiment of the invention the locking device comprises a rotatable lever. Preferably, the rotatable lever is integrated in a handle such that the locking device can be realized without requiring additional space.

According to a further embodiment of the invention the positioning arm is formed integrally with the aiming device. This may provide the advantage, that there is no additional effort necessary in order to provide a rigid and mechanically reliable connection between the positioning arm and the aiming device. Furthermore, an accidentally wrong assembly of the aiming device with the positioning arm may be effectively prevented.

According to a further embodiment of the invention the positioning arm is adapted to be detachably connected to the aiming device. This may provide the advantage that the aiming device can be formed separately from the positioning arm. It is clear that in this case, one has to ensure that a rigid and mechanically reliable connection between the positioning arm and the aiming device is provided.

A configuration wherein the positioning arm and the aiming device are formed as separate objects may provide the advantage that the implant, the adaptor device, the positioning arm and the aiming device can be included in a modular construction kit wherein each of these items is included in a variety of slightly different dimensions. Therefore, depending on the respective requirements the best combination of these items can be selected such that an optimal surgery may be accomplished.

According to a further aspect of the invention there is provided a medical system for detachably establishing a spatial orientation between a body implant and an aiming device, in particular between a bone stabilization implant and an aiming device for anchoring the implant to an internal part of a body. The medical system comprises an adapter device according to an embodiment described above. The medical system further comprises a positioning arm according to an embodiment described above.

According to a further aspect of the invention there is provided a method for detachably establishing a spatial orientation between a body implant and an aiming device, in particular between a bone stabilization implant and an aiming device for anchoring the implant to an internal part of a body. The method comprises the steps of
(a) bringing together a positioning arm and an adaptor device in such a manner that an engagement element of the positioning arm is coupled to an attachment element such that the positioning arm is hooked into the adaptor device,
(b) rotating the positioning arm relative to the adaptor device towards a final angular position, and
(c) intervening a snapping mechanism of the positioning arm in an interlocking element of the adaptor device.

This aspect of the present invention is based on the idea that a surgeon may establish a stable and reliable mechanical contact between the positioning arm and the adaptor device by means of a simple movement of his hand. Thereby, it is only necessary to perform a small rotational or swiveling movement of the positioning arm with respect to the adaptor device in order to allow for a mechanical snapping in connection between the positioning arm and the adaptor device.

According to a further embodiment of the invention the step of intervening occurs automatically when the positioning arm approaches the final angular position. This makes it in particularly easy for a surgeon to establish the stable and reliable mechanical contact between the positioning arm and the adaptor device such that it is unnecessary to perform an extra movement of the hand in order to provide a firm mechanical connection between the positioning arm and the adaptor device.

According to a further embodiment of the invention the method further comprises the step of locking the snapping mechanism by means of a locking device. This embodiment has the advantage that an unintentional opening of the mechanical connection between the snapping mechanism and the interlocking element may be prevented in an easy and effective way.

After a medical procedure employing the aiming device has been accomplished the positioning arm can easily be removed from the adaptor device and/or from the implant by simply removing or by simply opening the locking device. Such a medical procedure can comprise for instance boring holes in a bone with the help of a drilling jig being part of the aiming device.

According to a further embodiment of the invention the step of locking the snapping mechanism comprises rotating a lever. The rotatable lever may be integrated in a handle such that the locking device can be realized without requiring additional space. Therefore, the positioning arm does not comprise sharp edges and corners, which could bear the risk that internal tissue of a patient is damaged.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless other notified, in addition to any combination of features belonging to one subject matter also any combination between features relating to different subject matters, in particular between features of the apparatus type claims and features of the method type claims is disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

BRIEF DESCRIPTION OF THE DRAWINGS

The illustrations in the drawings are schematical. It is noted that in different drawings, similar or identical elements are provided with the same reference signs or with reference signs, which are different from the corresponding reference signs only within the first digit.

DETAILED DESCRIPTION

Figure 1A:
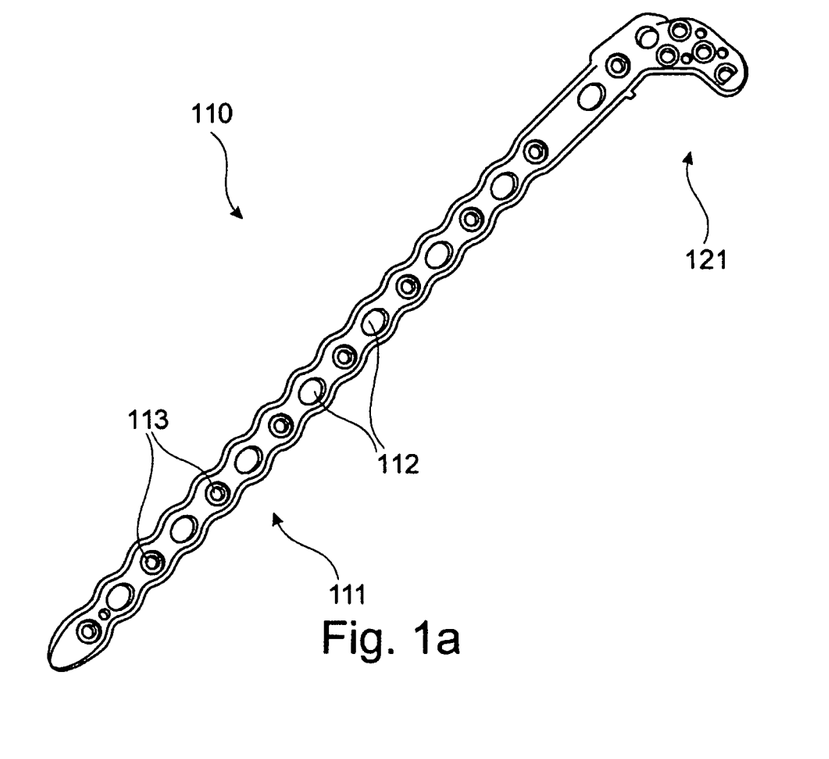
FIGS. 1a to 1e show different views of a bone stabilizing plate including an integrally formed adaptor device.

As can be seen from FIG. 1a, a bone stabilizing plate 110 comprises a lower portion 111 and an upper portion 121. The upper portion 121 represents an adaptor device 121, which is designed in such a manner that a firm mechanical connection between the plate 110 and a positioning arm may be established very easily.

The bone stabilizing plate comprises a plurality of openings 112 and a plurality of through holes 113. The openings are formed in the plate portion 111 in order to reduce both the weight and the material expenses of the plate portion 111, respectively. The through holes 113 may be used for inserting screws (not depicted) for fixing the plate portion 111 to a bone or to a bone fragment such that all parts of the bone are attached to the bone stabilizing plate portion 111.

Figure 1B:
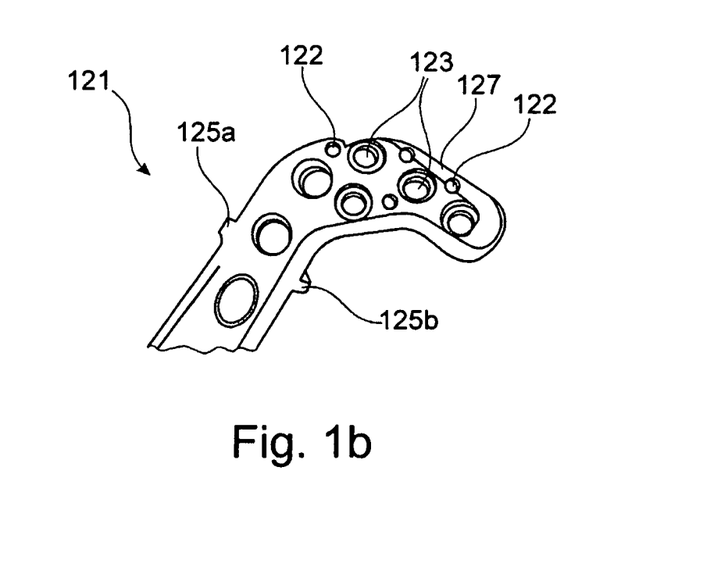

FIG. 1b shows an enlarged view of the adaptor device 121. The adaptor device 121 has a body 126 which comprises also some openings 122 and some through holes 123, which may be used for the same purposes as the openings 112 and as the plurality of through holes 113 shown in FIG. 1a, respectively.

The upper part 121 of the plate 110 is bent such that the plate 110 may be abutted against a broken bone along the full length of the bone including the bone end, e.g. the proximal tibia and the distal femur.

The adaptor device 121 comprises two attachment elements, a first attachment element 125a and a second attachment element 125b. The two attachment elements are formed as projections salient from body 126 of the adaptor device 121. The adaptor device 121 further comprises an interlocking element 127 having the form of an edge. As will be described later on, the attachment elements 125a and 125b and the interlocking element 127 may provide both a stable three-point bearing and a secure detachable connection between a positioning arm and the plate 110.

Figure 1C:
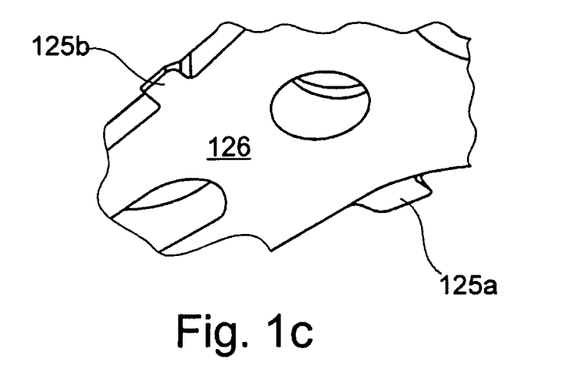

FIG. 1c shows the two attachment element 125a and 125b sticking out from the body 126 of the adaptor device 121.

Figure 1D:
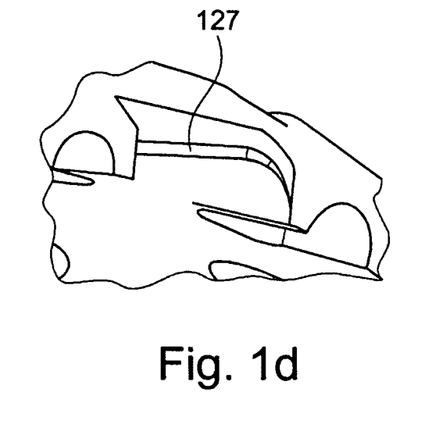

FIG. 1d shows the interlocking element 127, which according to the embodiment shown here is formed almost at the most upper section of plate 110. The edge of the interlocking element 127 can be described by a recess which is open to the bone contacting surface of the plate 110 and which extends inwardly from the plate edge and upwardly towards the top surface of the plate.

Figure 1E:
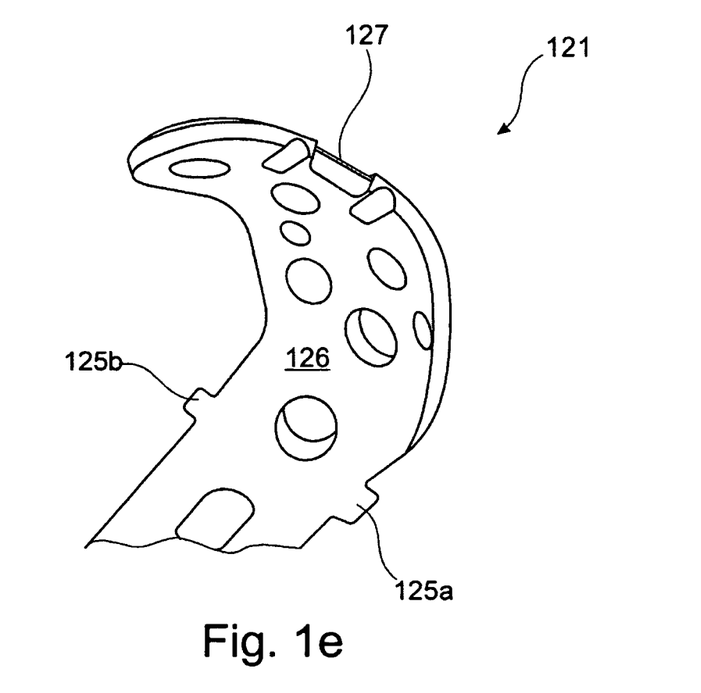

FIG. 1e shows a further view of the adaptor device 121. The two attachment elements 125a and 125b are formed as projections protruding from the body 126. The interlocking element 127 is formed as a more or less sharp edge at the outer circumference of the adaptor device 121. The adaptor device 121 comprises an asymmetric shape wherein the interlocking element 127 is formed slightly off a longitudinal axis of plate portion 111.

Figure 2A:
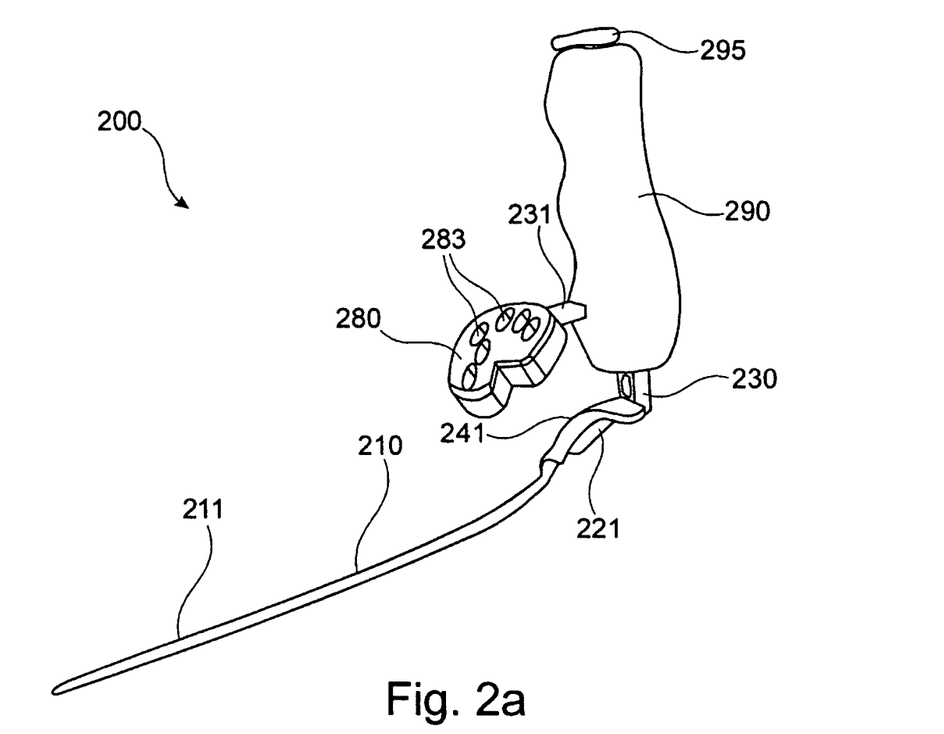
FIGS. 2a to 2d show different views of a bone stabilizing medical system according to an exemplary embodiment of the invention.

FIG. 2a shows a general view of a medical system 200 according to an embodiment of the invention. The medical system 200 allows for a convenient care of a broken bone by means of the bone stabilizing plate 210, which comprises a lower portion 211 and an upper portion 221. The upper portion 221 represents an adaptor device, which allows a positioning arm 230 to be detachably but firmly connected to the plate 210.

The positioning arm 230 comprises a lower portion 241 and an upper arm portion 231. The lower portion represents a contact portion 241, which is adapted to be detachably and firmly connected to the adaptor device 221.

The positioning arm 230 further comprises a handle 290. The handle 290 is formed in an ergonomic manner such that the positioning arm 230 may be moved manually in an easy and convenient manner. The handle is equipped with a rotatable lever 295, which is mechanically coupled to a locking device. The locking device will be described later on in connection with the FIGS. 3a to 3g.

The upper portion 231 of the positioning arm 230 represents a holder for aiming device 280. The aiming device 280 represents a drilling jig comprising through holes 283 for a precise and easy pre-drilling of holes into a bone fragment, which is located directly beneath the upper portion 221 of the bone stabilizing plate 210. Thereby, a minimal invasive and percutaneous surgery technique may be realized.

Figure 2B:
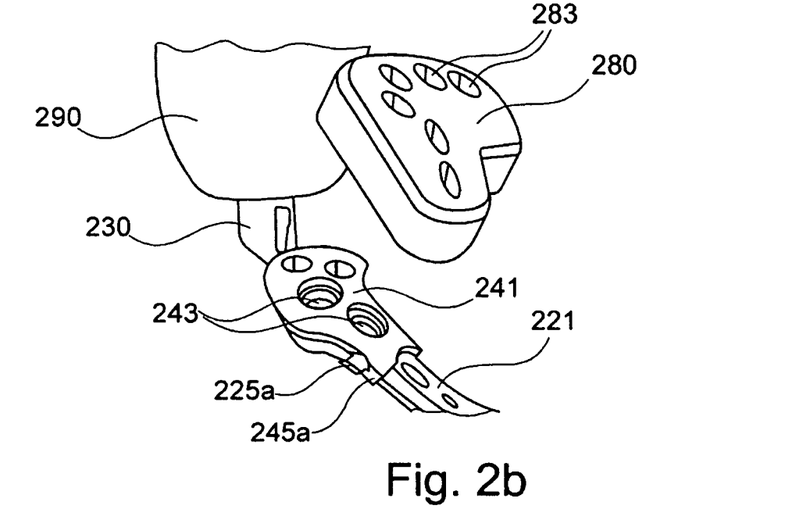

FIG. 2b shows an enlarged view of the connection portion between the positioning arm 230 and the adaptor device 221. The contact portion 241 of the positioning arm 230 comprises holes 243. These holes 243 represent openings such that a drill tool may be passed through the contact portion 241 in order to pre-drill holes in a bone fragment located directly beneath the adaptor device 221. The holes 243 have a diameter, which is bigger than the diameter of the through holes 123 in the adapter device 121 (see FIG. 1b). This makes it possible that screws, which are used for fixing the adaptor device 221 to the bone section located beneath the adaptor device 221, may be passed through the holes 243 formed in the contact portion 241.

At the lower end the contact portion 241 there are provided with two engaging elements, a first engaging element 245a and a second engaging element, respectively. The second engaging element cannot be seen in the view shown in FIG. 2b. According to the embodiment described here the engaging elements are formed as two notches, a first notch 245a and a second notch, respectively. The two notches have such a shape that the contact portion 241 of the positioning arm 230 may be hooked into the two attachment elements, the first attachment element 225a and the second attachment element, respectively.

Figure 2C:
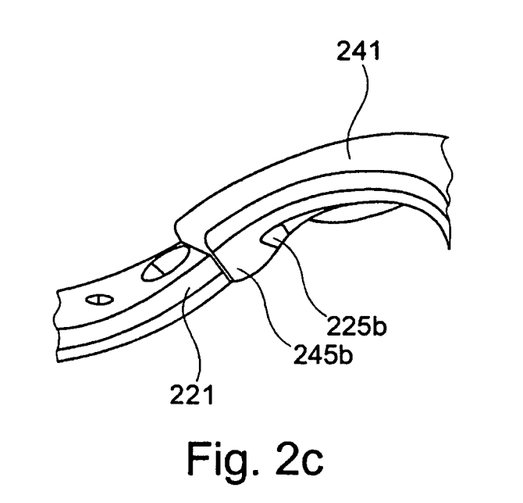

FIG. 2c shows a further enlarged view of the connection portion between the contact portion 241 of the positioning arm 230 and the adaptor device 221. In this view the second engaging element (second notch) 245b can be seen as it hooks into the second attachment element (second projection) 225b.

Figure 2D:
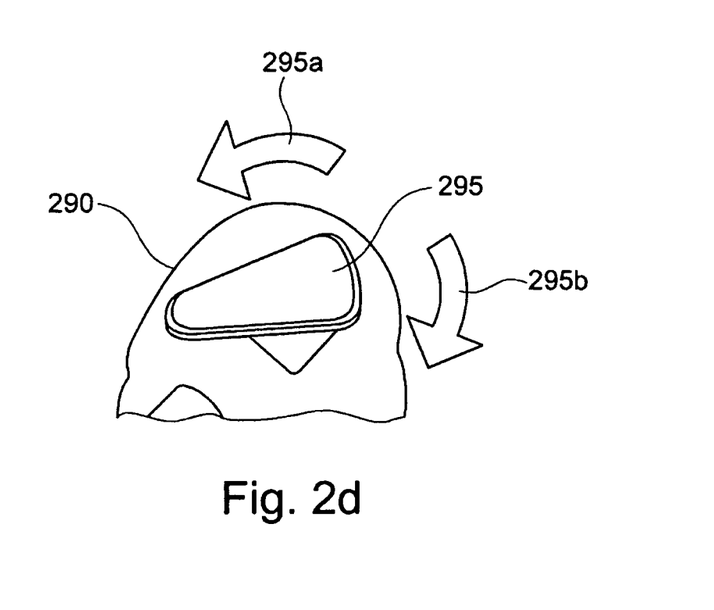

FIG. 2d shows a top view of the handle 290. On top of the handle 290 there is provided a small lever 295. The lever 295 can be rotated in a clockwise direction 295b for interlocking the detachable connection between the adaptor device 221 of the bone stabilizing plate 210 and the positioning arm 230 representing a mechanical holder for the aiming device 280. The lever 295 can also be rotated in a counterclockwise direction 295a in order to release the interlocking device such that the positioning arm 230 can be removed from the bone stabilizing plate 210.

Figure 3A:
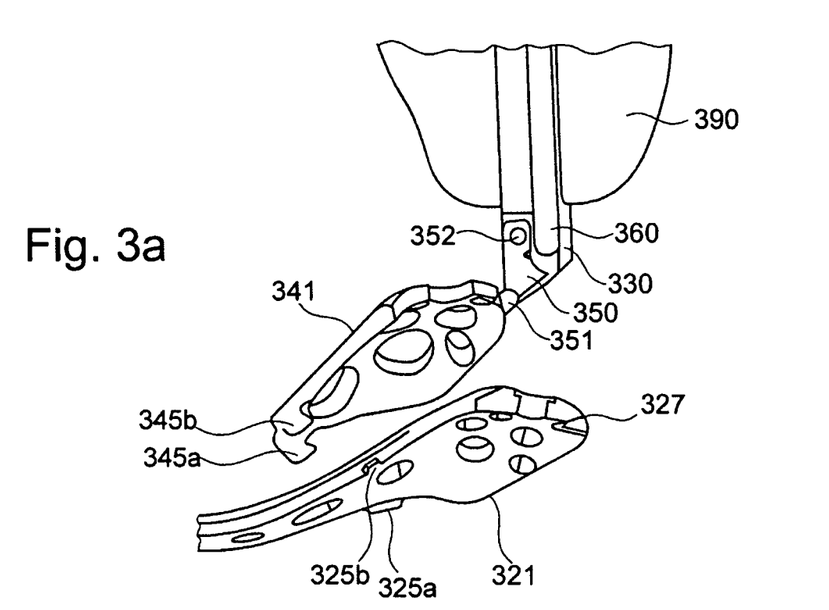
FIGS. 3a to 3n illustrate the procedure for establishing a firm mechanical connection between the positioning arm and the adaptor device.
Figure 3B:
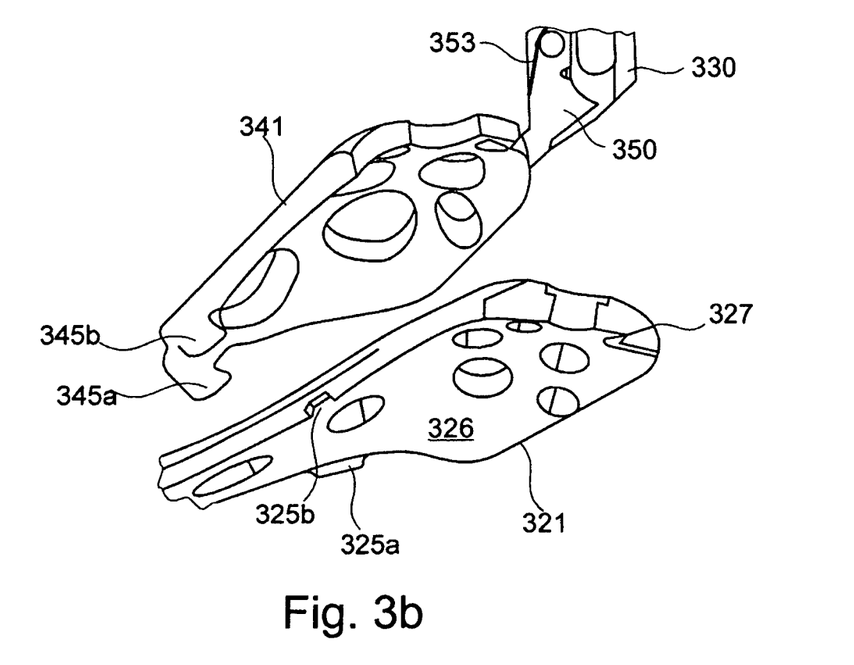
Figure 3C:
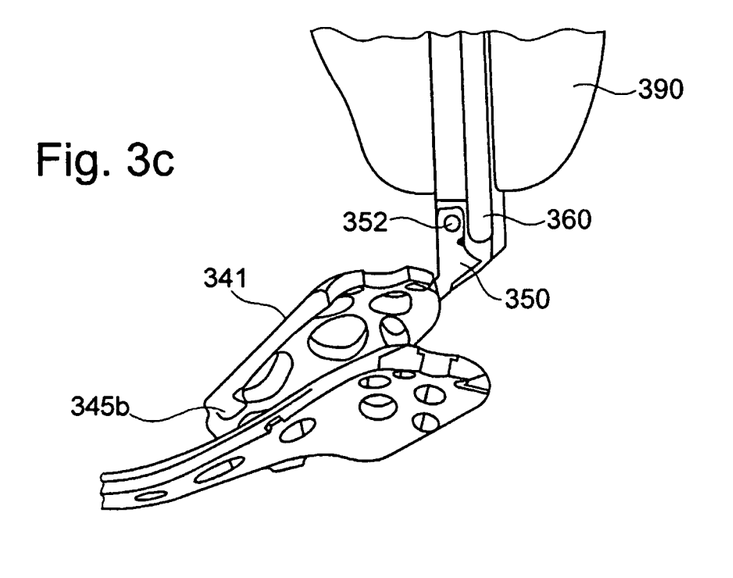
Figure 3D:
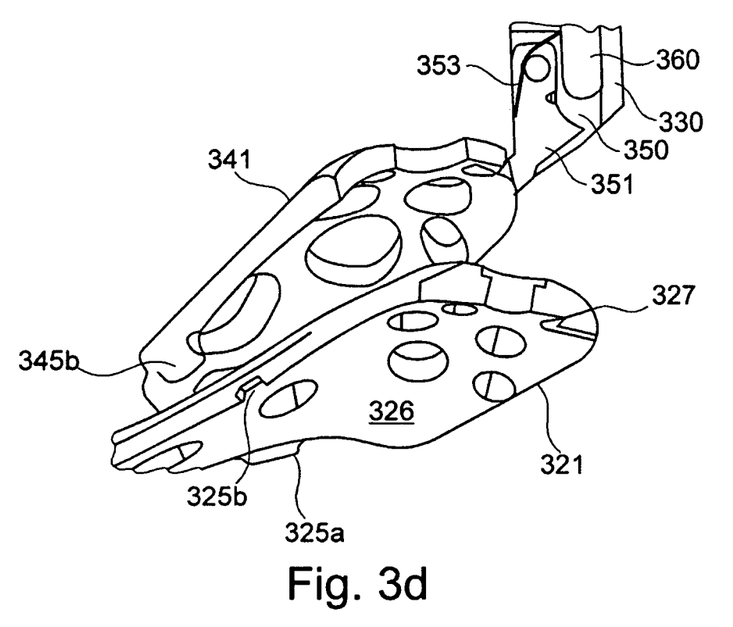
Figure 3E:
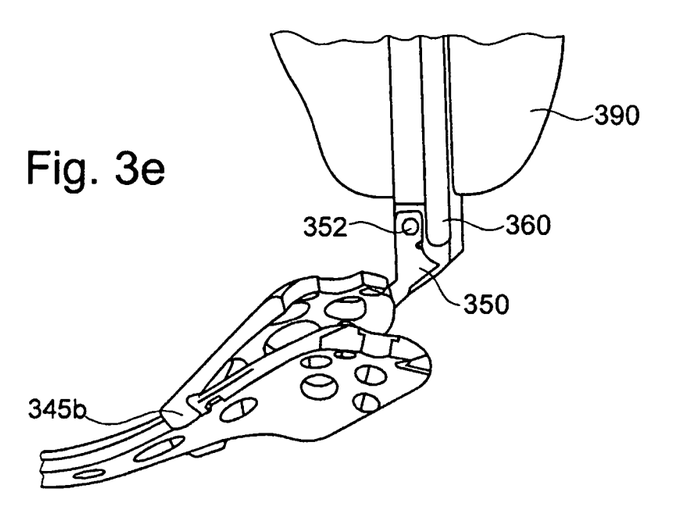
Figure 3F:
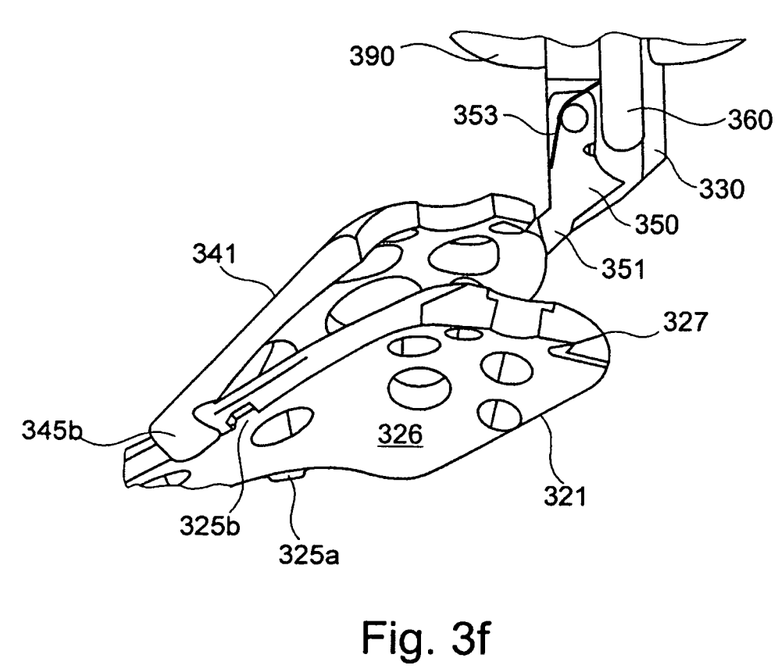
Figure 3G:
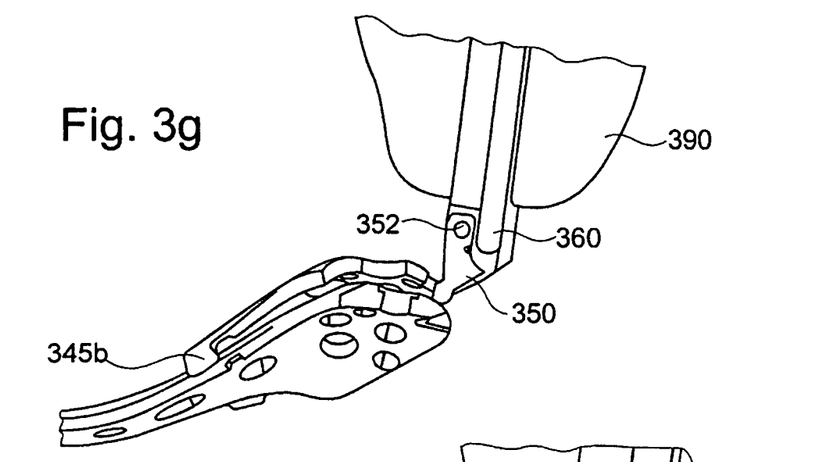
Figure 3H:
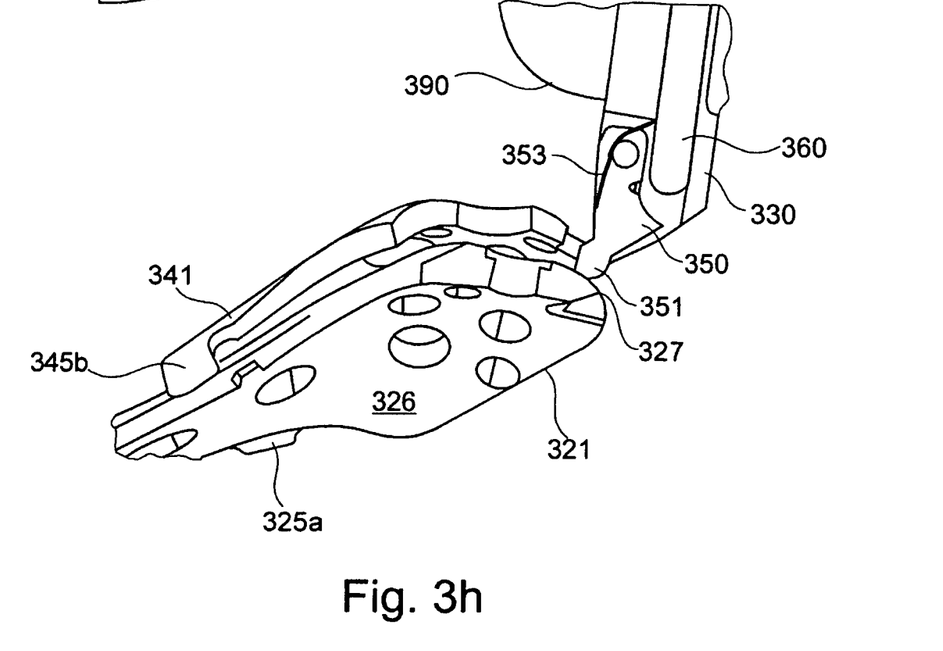
Figure 3I:
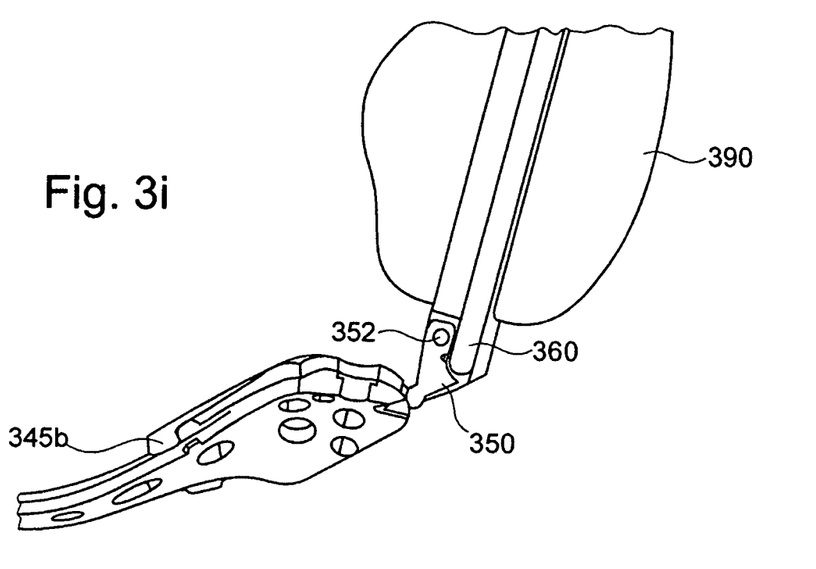
Figure 3J:
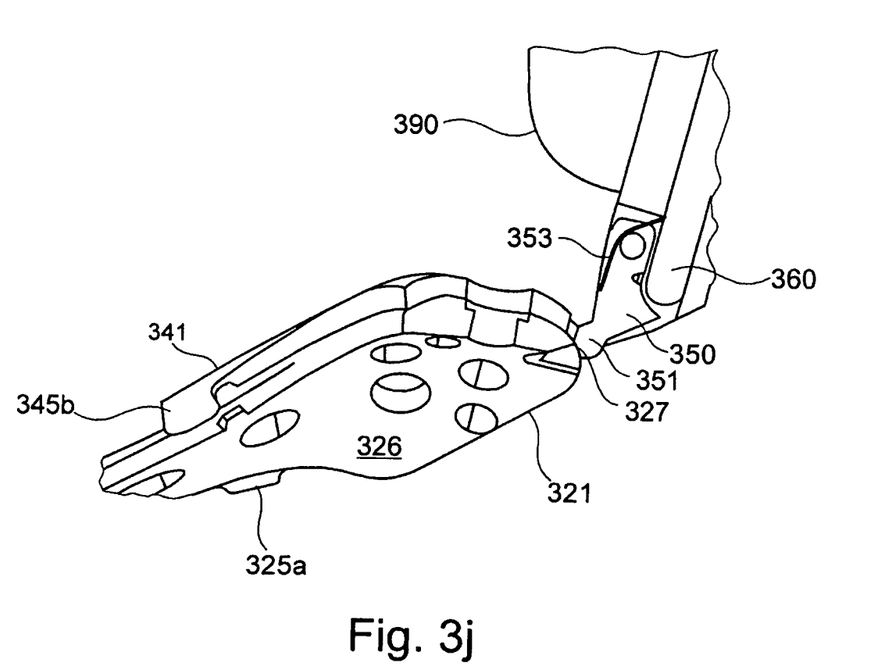
Figure 3K:
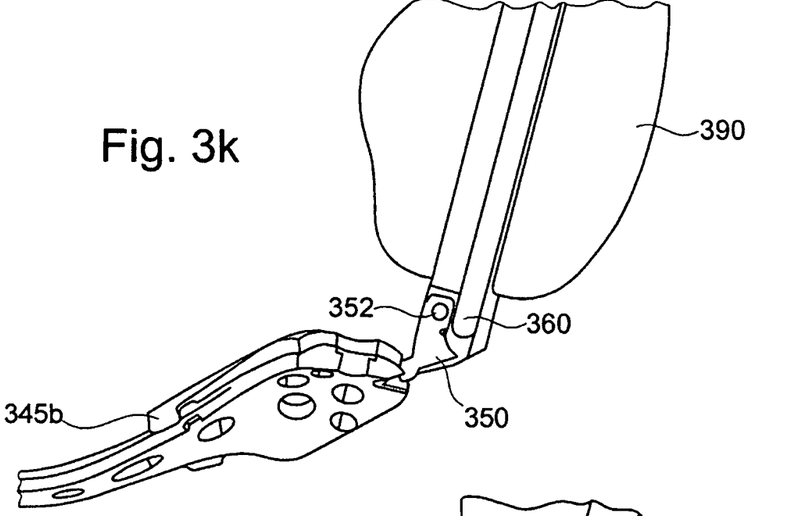
Figure 3L:
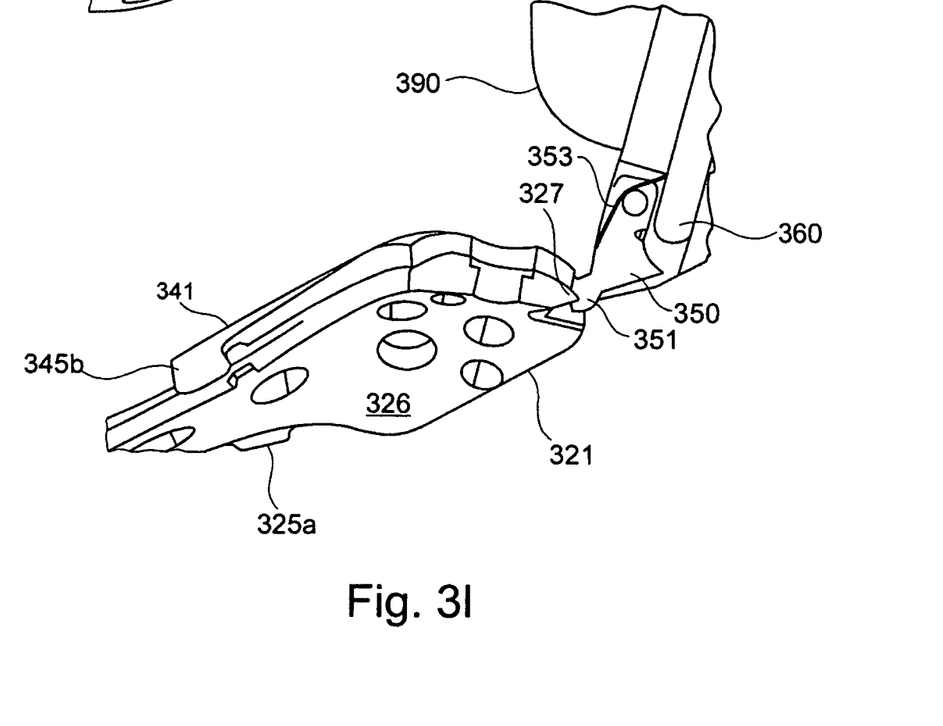
Figure 3M:
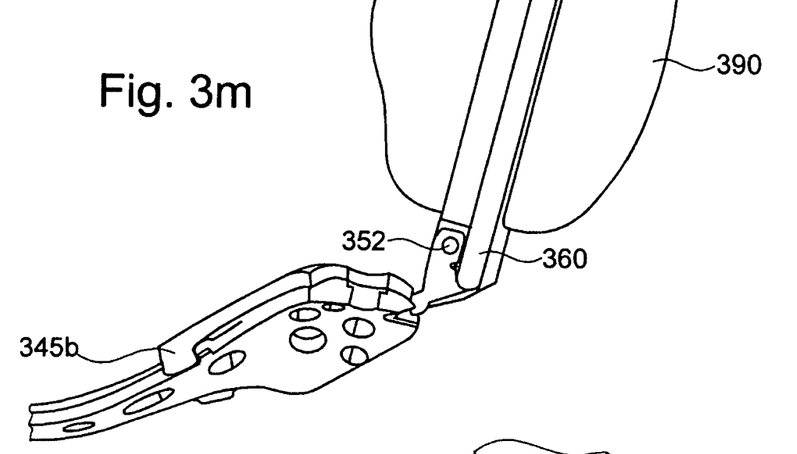
Figure 3N:
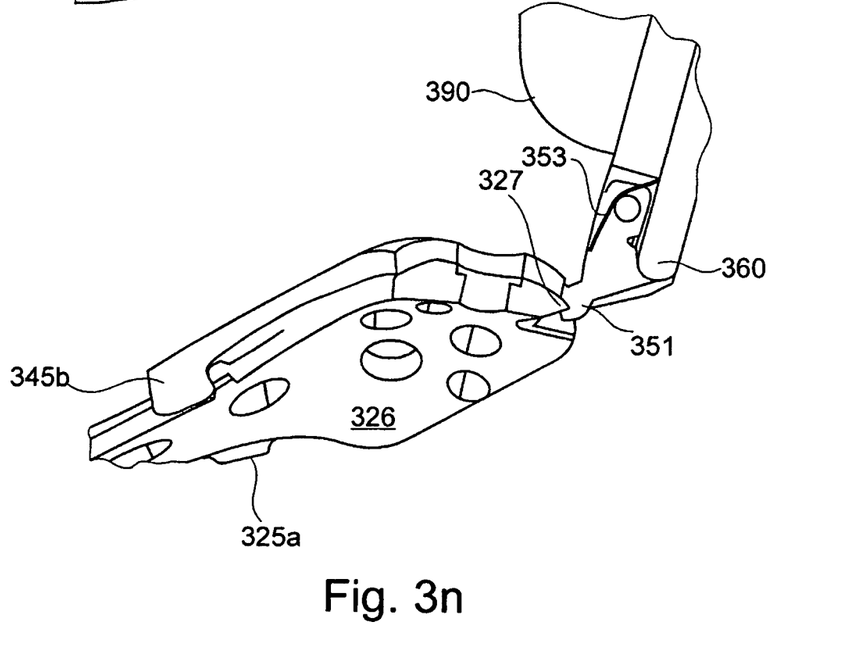

FIGS. 3a to 3n show a sequence of views illustrating the procedure of establishing a firm mechanical connection between the contact portion 341 of the positioning arm 330 and the adaptor device 321. FIGS. 3a, 3c, 3e, 3g, 3i, 3k and 3m show a general view of the relative orientation between the contact portion 341 and the adaptor device 321. FIGS. 3b, 3d, 3f, 3h, 3j, 3l and 3n each show a corresponding enlarged view.

As can be seen from FIGS. 3a and 3b, an operator (not shown) moves the contact portion 341 towards the adaptor device 321 in an appropriate orientation such that the first hook 345a and the second hook 345b hooks into the first projection 325a and the second projection 325b, respectively. The two projections 325a and 325b extend out from the body 326 of the adaptor device 321.

The positioning arm 330 is provided with a snapping mechanism 350, which is rotatable with respect to a pivot 352 within small angular limits. The snapping mechanism 350 is provided with a spring 353 such that the snapping mechanism 350 is kept in the initial angular position shown in FIG. 3a.

The snapping mechanism 350 comprises a hook type element 351, which is integrally formed with the snapping mechanism 350. The function of the snapping mechanism 350 will be described below.

The positioning arm 330 is further provided with a locking device 360. According to the embodiment described herein the locking device is a rod 360, which is mechanically coupled to the lever 295 shown in FIG. 2d. As can be seen, the locking rod 360 is capable of seizing the snapping mechanism 350, when the locking rod 360 is moved downwards such that it touches the snapping mechanism 350. The locking rod 360 is mechanically coupled to the lever 295 such that, when the lever 295 is rotated clockwise, the locking rod 360 moves downward. When the lever 295 is rotated counter clockwise the locking rod 360 moves upward. The man skilled in the art will find various appropriate solutions in order to realize the described mechanical coupling between the lever 295 and the locking rod 360.

The adaptor device 321 is provided with the interlocking element 327 having the form of an edge. As can also be seen from FIG. 3a, the snapping mechanism 350 is adapted to engage in the interlocking element 327, when the contact portion 341 and the adaptor element 321 are abutted against each other.

In order to establish a detachable connection between the contact portion 341 and the adaptor element 321, the positioning arm 330 is manually moved towards the adaptor element 321. This is depicted in FIGS. 3c and 3d.

As can be seen from FIGS. 3e and 3f, the contact portion 341 is further moved towards the adaptor element 321, such that the two notches 345a and 345b hook into the two projections 325a and 325b, respectively.

As can be seen from FIGS. 3g and 3h, the positioning arm is pivotally rotated around an axis which is defined by the two regions wherein the two attachment elements 325a and 325b and the two engaging elements 345a and 345b abut against each other, respectively. Thereby the snapping mechanism 350 and the interlocking element 327 approach towards each other. When the hook type element 351 of the snapping mechanism 350 abuts against an upper side of the interlocking element 327 the snapping mechanism 350 will be pulled to the side.

FIGS. 3i and 3j show the contact portion 341 and the adaptor element 321 when abutted against each other. However, the snapping mechanism 350 has not yet been moved back in its normal position.

FIGS. 3k and 3l show the contact portion 341 and the adaptor element 321, which are fastened to each other by means of the snapping mechanism 350. Due to an elastic force powered by the spring 353 the snapping mechanism 350 has been moved back in its normal position. Thus, the contact portion 341 and the adaptor element 321 are secured to each other by means of a three-point bearing. The three-point bearing includes the connection between the snapping mechanism 350 and the interlocking element 327 and the two regions wherein the two attachment elements and the two engaging elements abut against each other, respectively. Thereby, a precise orientation between the plate 210 and the aiming device 280 may be established (see FIG. 2a).

FIGS. 3m and 3n show a locked state of the snapping mechanism 350. The locked state is characterized by the fact that an accidental and unwanted opening of the snapping mechanism 350 can be reliably prevented. Thereby, the locking rod 360 is moved downwards such that the lower end of the rod 360 engages in the snapping mechanism 350.

When the snapping mechanism 350 is in the locked state the bone stabilizing plate respectively the adaptor device 321 and the aiming device respectively the positioning arm 330 represent a stiff medical system. Therefore, a surgeon may grab the medical system at the handle 390 and position the plate on a broken bone of a patient. The aiming device allows for a precise pre-drilling of holes within the bone tissue, wherein the predrilled holes align with predetermined holes within the bone stabilizing plate. Thereby, the aiming device works like a drilling jig. After having completed the pre-drilling, threaded screws, driven into the bone tissue in order to stabilize the bone in its normal position.

After the plate has been fixed to the broken bone the positioning arm, including the aiming device, has to be removed from the fixed plate in order to allow for a closing of the operation.

In order to remove the positioning arm from the bone plate one has to detach the contact portion 341 from the adaptor element 321. First the locking rod 360 has to be moved upwards. Then, the positioning arm is rotated slightly counter clockwise such that the snapping mechanism 350 glides off the interlocking element 327. The detaching of the contact portion 341 from the adaptor element 321 can be completed be carrying out the above described procedure in a reversed order.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An adaptor device for detachably establishing a spatial orientation between a bone stabilization implant and an aiming device for anchoring the implant to an internal part of a body, the adaptor device comprising:

a positioning arm having first and second hook shaped engaging elements and a snapping connector element;
an adaptor device body comprising:
a first attachment element, including a first protrusion with a contact surface extending outwardly from the device body wherein the first hooked shaped engaging element of the positioning arm can be hooked onto the first protrusion of the adaptor device allowing for rotational engagement between an inner surface of the first hook of the positioning arm and the first protrusion contact surface;
a second attachment element having a second protrusion with a contact surface extending outwardly from the adaptor device body wherein the second hook shaped engaging element of the positioning arm can be hooked into the second protrusion of the adaptor device allowing for rotational engagement between an inner surface of the second hook of the positioning arm and the second protrusion contact surface wherein an axis extends between the first protrusion contact surface and the second protrusion contact surfaces with the hook shaped engaging elements partially encircling the axis when hooked onto the first and second protrusions, and
the adaptor device body including an interlocking element positioned intermediate the first and second-protrusions, wherein the snapping connector element of the positioning arm automatically engages in the interlocking element when the positioning arm and the first and second hooked shaped elements are rotated relative to the adaptor device about the axis between the first and second protrusions contact surfaces towards a final angular position.

2. The adaptor device according to claim 1, wherein the interlocking element comprises an edge.

3. The adaptor device according to claim 1, wherein the first and second attachment elements are located on opposite sides of the adaptor device body.

4. The adaptor device according to claim 1, wherein the adaptor device body is a part of a one-piece implant.

5. The adaptor device according to claim 1, wherein the adaptor device body is a part of a one-piece plate which is used for a bone stabilization.

6. The adaptor device according to claim 1, further comprising a handle for facilitating a manual rotation of the positioning arm with respect to the adaptor device body.

7. The adaptor device according to claim 1, further comprising a locking device, adapted to lock the snapping connector element.

8. The adaptor device according to claim 7, wherein the locking device comprises a rotatable lever.

9. The adaptor device according to claim 1, wherein the positioning arm is part of a one-piece aiming device.

10. The adaptor device according to claim 1, wherein the positioning arm is adapted to be detachably connected to an aiming device.

11. An adaptor device for connecting a bone plate to a positioning arm of an aiming device comprising:
a positioning arm having hook-shaped elements and a snapping mechanism;
a body having an outwardly facing surface, a bone contacting surface and an outer side surface connecting the outwardly facing surface to the bone contacting surface, first and second spaced protrusions each having a contact surface extending outwardly of the body from the outer side surface, the protrusions for engaging the hook-shaped elements located on the positioning arm, the hook-shaped elements each having an inner surface for rotationally engaging a respective contact surface of protrusions, wherein an axis extends between the first protrusion contact surface and the second protrusion contact surface with the hook-shaped engaging elements partially encircling the axis when hooked onto the first and second protrusions; and
an interlocking element formed on the outer side surface of the body intermediate the first and second spaced protrusions, the interlocking element including a recess open towards the bone contacting surface of the body forming a ledge at the outwardly facing surface of the body, the interlocking element for engaging the snapping mechanism located on the positioning arm.

12. The adaptor device of claim 11 wherein the body is formed as a part of a one-piece elongated bone plate and the interlocking element is offset with respect to a center longitudinal axis of the bone plate.

13. The adaptor device of claim 11 wherein the body forms an enlarged end of the bone plate.

14. The adaptor device of claim 11, wherein the body is a part of a one piece bone plate.

15. An adaptor device for detachably establishing a spatial orientation between a bone stabilization implant and an aiming device for anchoring the implant to an internal part of a body, the adaptor device comprising:
a positioning arm having first and second hook shaped elements and a spring loaded snapping mechanism;
an adaptor device body having a bone facing surface and outwardly facing surface connected by a side surface, first and second spaced protrusions each having a contact surface extending outwardly of the body from the side surface along an axis wherein the first and second hook shaped elements of the positioning arm engage the first and second protrusions, the hook-shaped elements each having an inner surface for rotationally engaging a respective contact surface of protrusions, wherein an axis extends between the first protrusion contact surface and the second protrusion contact surface with the hook-shaped engaging elements partially encircling the axis when hooked onto the first and second protrusions; and
an interlocking element formed on the side surface intermediate the first and second protrusions, wherein the spring loaded snapping mechanism of the positioning arm engaging the interlocking element when the positioning arm, when hooked onto the protrusions of the adaptor device body, is rotated about the axis of the protrusions relative to the adaptor device body toward a final angular position, the spring loaded snapping mechanism rotatably mounted on the positioning arm is moved away from a surface of the interlocking element against a spring force upon rotation of the positioning arm towards a final position and engages the adaptor device interlocking element at the final position.

16. An adaptor device for connecting a bone plate to a positioning arm of an aiming device in a bone implant comprising:
a positioning arm having a spring loaded snapping mechanism;
a body having top and bottom surfaces connected by side surfaces, a first side surface with a first outwardly extending coupling element, a second side surface with a second outwardly extending coupling element, the first and second coupling element having a contact surface and an interlocking element in a side surface intermediate the first and second coupling elements, the first and second coupling elements respectively for engaging first and second hook elements on the positioning arm and the interlocking element engaging the snapping mechanism on the positioning arm, the hook-shaped elements each having an inner surface for rotationally engaging a respective contact surface of protrusions, wherein an axis extends between the first protrusion contact surface and the second protrusion contact surface with the hook-shaped engaging elements partially encircling the axis when hooked onto the first and second protrusions, the snapping mechanism on the positioning arm including a spring loaded clamp element rotatably mounted on the positioning arm selectively engaging an underside of a surface of the interlocking element, the clamp element movable against the spring upon rotation of the positioning arm towards the body when the coupling elements and the hook elements are engaged.

* * * * *